(12) United States Patent
Hess et al.

(10) Patent No.: US 8,020,973 B2
(45) Date of Patent: Sep. 20, 2011

(54) METHOD OF MANUFACTURING A LIQUID DROPLET SPRAY DEVICE AND SUCH SPRAY DEVICE

(75) Inventors: Joseph Hess, Bevaix (CH); Jean-Marc Flick, Savagnier (CH); Hu Bo, Neuchatel (CH); Philippe Luginbuhl, Nods (CH); Raphael Weber, La Chaux-de-Fonds (CH)

(73) Assignee: EP Systems SA, Neuchâtel (CH)

( * ) Notice: Subject to any disclaimer, the term of this patent is extended or adjusted under 35 U.S.C. 154(b) by 271 days.

(21) Appl. No.: 10/468,827

(22) PCT Filed: Feb. 25, 2002

(86) PCT No.: PCT/EP02/01945
§ 371 (c)(1),
(2), (4) Date: Feb. 6, 2004

(87) PCT Pub. No.: WO02/068128
PCT Pub. Date: Sep. 6, 2002

(65) Prior Publication Data
US 2004/0124173 A1     Jul. 1, 2004

(30) Foreign Application Priority Data

Feb. 23, 2001 (EP) .................................. 01103653

(51) Int. Cl.
*B41J 2/045* (2006.01)
(52) U.S. Cl. ............................................. 347/68
(58) Field of Classification Search .............. 347/55, 347/68
See application file for complete search history.

(56) References Cited

U.S. PATENT DOCUMENTS

| | | | | | |
|---|---|---|---|---|---|
| 5,462,839 | A | * | 10/1995 | de Rooij et al. | 430/320 |
| 5,612,725 | A | * | 3/1997 | Okimoto | 347/71 |
| 5,635,337 | A | | 6/1997 | Bartha et al. | |
| 5,872,582 | A | * | 2/1999 | Pan | 347/65 |

(Continued)

FOREIGN PATENT DOCUMENTS

EP    0 516 565  B1    4/1996

(Continued)

OTHER PUBLICATIONS

European Search Report, completed May 29, 2002, mailed Jun. 10, 2002, by E. Daintith.

(Continued)

*Primary Examiner* — Laura E Martin
(74) *Attorney, Agent, or Firm* — Griffin & Szipl, P.C.

(57) ABSTRACT

The invention concerns a liquid droplet spray device for atomising a liquid substance, Its housing consists of a at least a first substrate (15), a space (12) within the housing for containing the supplied liquid substance, an outlet means arranged in the first substrate (15) and comprising at least one outlet nozzle (19) and at least one output channel (20), said output channel (20) having straight side-walls, and a vibrating element (18) for vibrating the liquid so as to eject it. According to the present invention, each output channel (20) has a stepped shape having a lower portion (20*a*) and an upper portion (20*b*), the lower portion being arranged adjacent the space (12) and being of larger diameter than the upper portion (20*b*). The outlet nozzle (19) of each output channel is straight and does not show notching effects. The invention also concerns a method of manufacturing such device using a differential etching technique to obtain the stepped shape output channel without notching effects on the outlet nozzle.

30 Claims, 5 Drawing Sheets

U.S. PATENT DOCUMENTS

Figure 3A:
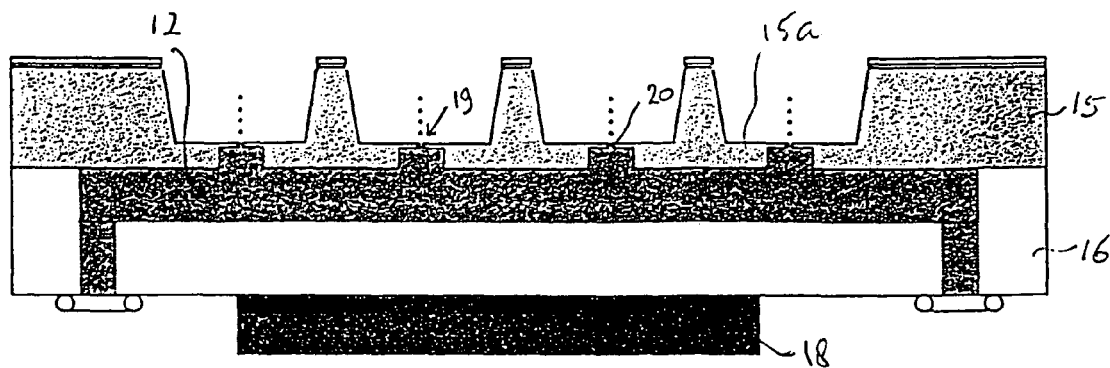

| | | | |
|---|---|---|---|
| 5,962,955 A * | 10/1999 | Tsukada et al. | 310/366 |
| 5,963,230 A * | 10/1999 | Higashino et al. | 347/40 |
| 6,039,440 A * | 3/2000 | Osawa et al. | 347/70 |
| 6,142,607 A * | 11/2000 | Takata et al. | 347/47 |
| 6,523,762 B1 * | 2/2003 | Luginbuhl et al. | 239/589 |

FOREIGN PATENT DOCUMENTS

| | | |
|---|---|---|
| EP | 0 923 957 A1 | 6/1999 |
| EP | 0 985 534 A1 | 3/2000 |
| EP | 1 005 916 A1 | 6/2000 |
| EP | 1 005 917 A1 | 6/2000 |
| EP | 1005917 A1 * | 6/2000 |
| EP | 1 046 917 A2 | 10/2000 |
| EP | 1129741 A2 * | 9/2001 |
| WO | WO 95/15822 | 6/1995 |
| WO | WO 00/06388 | 2/2000 |

OTHER PUBLICATIONS

Exhibit A1, Webster's New Collegiate Dictionary, pp. 801 (1977).
Exhibit A2, Computer Professional's Dictionary, pp. 84, 261 and 269 (1990).

* cited by examiner

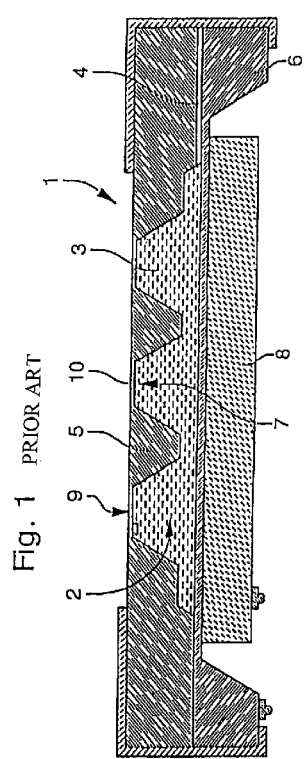
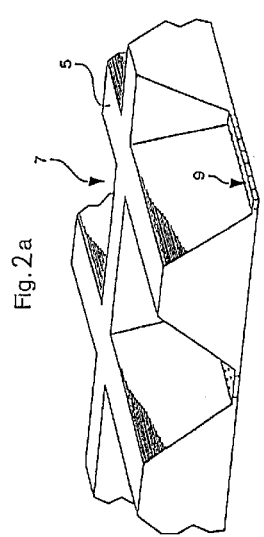
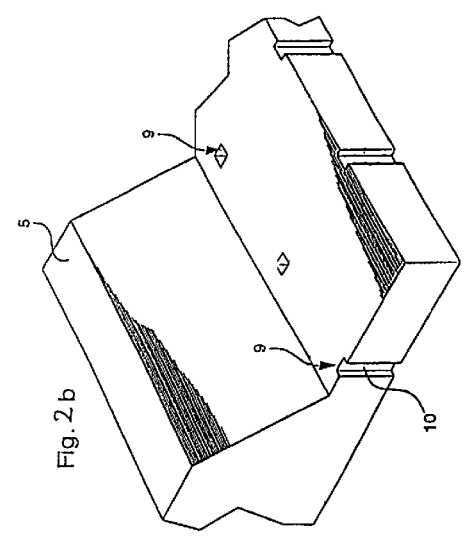
Fig. 1 PRIOR ART
Fig. 2a
Fig. 2b

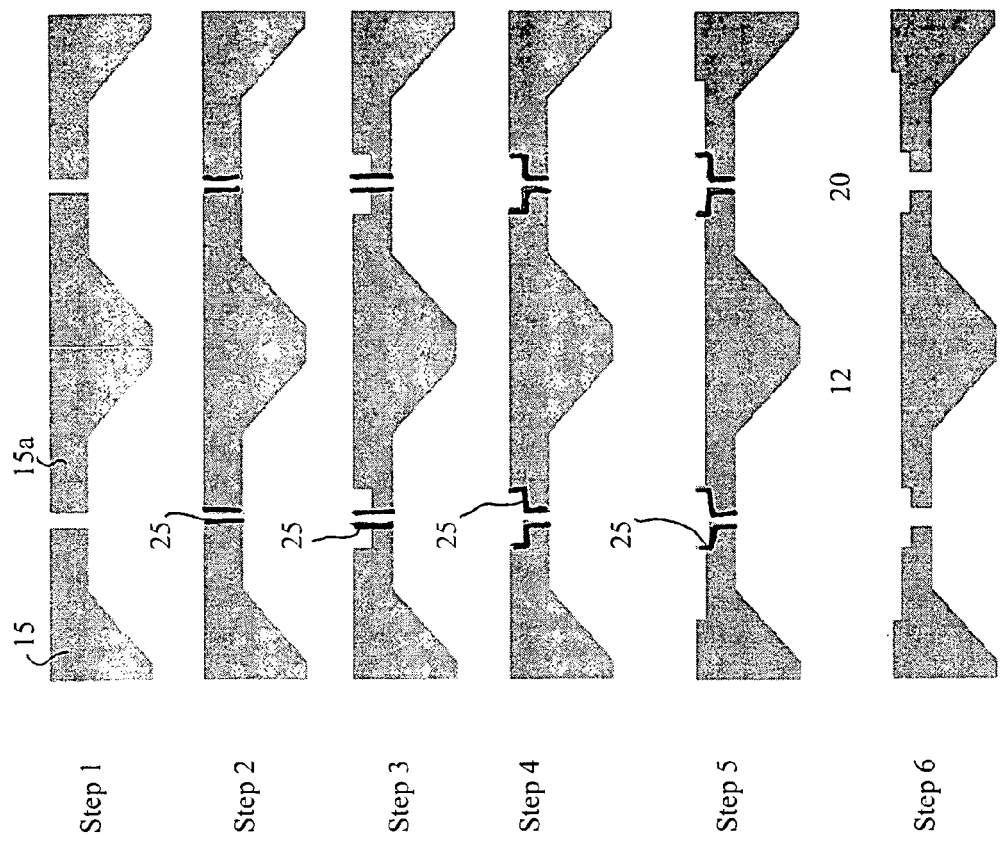
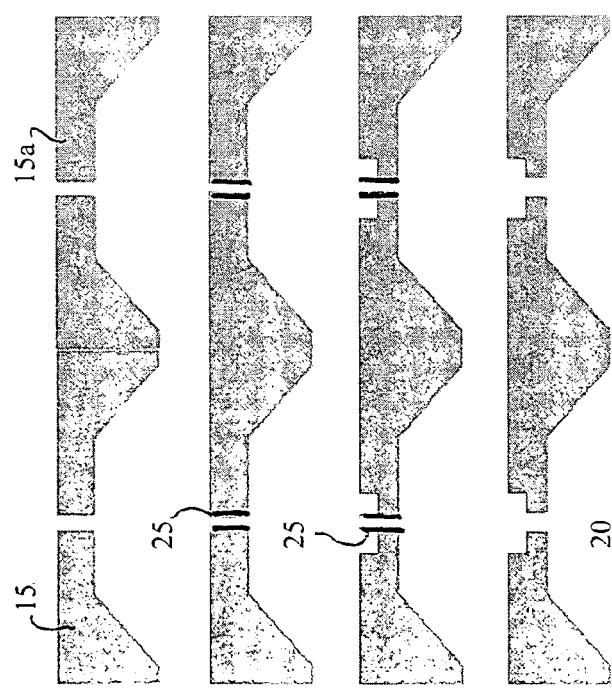

METHOD OF MANUFACTURING A LIQUID DROPLET SPRAY DEVICE AND SUCH SPRAY DEVICE

This is a National Phase Application in the United States of International Patent Application No. PCT/EP02/01945, filed Feb. 25, 2002, which claims priority on European Patent Application No. EP 01 103 653.0, filed Feb. 23, 2001. The entire disclosures of the above patent applications are hereby incorporated by reference.

The present invention relates to a method of manufacturing a liquid droplet spray device suitable for atomising a liquid substance such as a drug, a fragrance or other aerosolised liquids, as well as the device thus obtained. Such a device may be used, e.g., for perfume dispensers, for inkjet printer heads, for deposition of an array or arrays of droplets on a surface, for fuel injection devices of an engine or for administrating a nebulized drug to a patient by means of his or her respiratory system. Such an administration device, in its simplest form, is commonly called an inhaler. It may be used, e.g., for the controlled administration of drugs or for a variety of therapies using nebulized drug administration including anaesthetics or during minimally invasive surgery. The device delivers the drug, which is in the form of a liquid substance, as a dispersion of atomised droplets. More specifically, the present invention concerns an improved liquid droplet spray device which efficiently creates and which fully expels a liquid droplet spray, as well as a method of manufacturing such.

Various devices are known for atomising a liquid. Document EP 0 516 565 describes an ultrasonic wave nebuliser which atomises water. This apparatus is used as a room humidifier. Vibration is transmitted through the water to the water surface from which the spray is produced. A perforate membrane is provided to retain the water in absence of oscillation.

Typically, inhaler devices use the same principle to atomise the liquid into droplets, see for example the document WO 95/15822.

Furthermore, the droplet size, which depends on the size of the outlet orifices of the perforate membrane, also depends on the vibration frequency. In order to obtain a small droplet, a very high frequency should be used, typically over 1 MHz for droplets of about 10 μm in diameter. This leads to increased power consumption due to the high frequency so that such a device is not suitable for a small battery operated device.

Another liquid droplet spray device is known from the document EP-A-0 923 957 and the document EP-A-1 005 916, both in the name of the present Applicant. A brief description of the liquid droplet spray device known from these documents, which are hereby incorporated by reference, is given here while referring to FIG. 1.

In this particular embodiment spray device 1 consists of a housing formed of a superposition of a first, or a top substrate 5 and a second, or a bottom substrate 6 in-between which a chamber or a space 2 is formed for containing a liquid substance 3 and thus providing a compression chamber. Top substrate 5 contains outlet means consisting of cavity or cavities 7 which can partly constitute space 2, outlet nozzles 9 and output channels 10 connecting these nozzles to space 2.

Liquid substance 3 enters spray device 1 by way of, e.g., a very low pressure, e.g., around a few millibar, or capillary action. This can be achieved for example by way of at least one input tube or needle 4 through which the liquid substance may be supplied from an external reservoir (not shown) into spray device 1. Spray device 1 further comprises a vibrating element 8, e.g. a piezoelectric element to cause vibration of liquid substance 3 in space 2.

The method of manufacturing this device is carried out by using technology known from the field of semiconductors. Thus, top and bottom substrates may be manufactured in a similar manner e.g. by etching a silicon wafer in a suitable manner, e.g. by wet or dry etching and by using one or more masks or by micro-machining Pyrex wafers. The substrates 5 and 6 are attached to each other, preferably by appropriate bonding technique, such as anodic bonding, so as to form and enclose space 2.

The method of manufacturing the output channel preferably comprises micro-machining the channel by using a deep reactive vertical plasma etching of silicon, e.g. at room temperature or low temperature, and an advanced silicon etch process so as to obtain highly-toleranced straight side-walls of the channel. These prior art documents further describe techniques allowing for such output channels with a straight, non-tapered profile. This provides for a precisely defined pressure drop, droplet size and flow behaviour across output channel 10 for aqueous solutions and suspensions whereas the relatively smooth surface is suited for medications carrying small solid particles, e.g. from less than 1 to approx 2 μm, in suspensions. The same effect can be obtained proportionally with larger dimensions, e.g. with nozzles of 10 μm or larger for example for perfume dispensing applications or in a practical variation of the cited prior art of the applicant by simply using the vertical plasma etching micro-machining method to produce an output channel whose cross-section is divided into two or more identical sub-channels to allow for an even finer control of pressure drop, droplet size and flow behaviour across said channel 10. The cross section of the vertical channel or channel section can be of a suitable geometrical form, e.g. circular, triangular or a suitable geometrical shape such as a cross when the channel consists of several identical sub-channels. The cross section of the cavities 7 can also be of suitable geometrical form or combination of forms.

FIG. 2*a* shows a schematic detailed view of the first, or top substrate of this prior art liquid droplet spray device. The top substrate is shown upside down with respect to FIG. 1 in a further practical variation of the cited prior art which has already been shown with an inversion of the bottom substrate, thus further reducing dead space. As can be seen, top substrate 5 comprises the cavities 7, output channels 10 and outlet nozzles 9. The top surface of the substrate-delimiting cavity 7 forms a membrane section in substrate 5. The surface of this membrane section is much larger than the actual nozzle surface, so that it is possible to provide several outlet nozzles 9 on the membrane surface in order to eject more droplets simultaneously. As already mentioned in the cited prior art, it is obvious that cavities 7 are not necessarily tapered but can be straight according to the manufacturing process chosen. FIG. 2*b* shows a close-up view of a part of FIG. 2*a* in which it can be seen that the output channels 10 and outlet nozzles 9 may be readily placed according to the specific conditions.

The diameter of a droplet depends on the nozzle hole size "d" for a given frequency of the vibration of the liquid substance and the inlet pressure. In this prior art device where a frequency of around 243 kHz is used, the mean droplet diameter has been found to be around 5 μm, the diameter of the hole of nozzle 9 is around 7 μm and the inlet pressure is a few millibars. One such a droplet thus contains a quantity of around 67 femtoliters ($10^{-15}$ l) so that as such the number of nozzles may be determined as a function of the amount to be ejected.

Indeed, the fabrication tolerance Δd of the outlet nozzles is an essential factor in controlling and determining the amount, i.e. the volume "V" of an expelled droplet. In fact, this volume V depends on $d^3$ ($V=⅙*\Pi d^3$), d being the diameter of the outlet nozzle. For example, if d=5 μm, and Δd=±0.5 μm, the droplet volume V may vary from 47.5 (d=4.5) to 87 (d=5.5) which is a variation of 83%.

Furthermore, it is known that the pressure drop across the output channel depends on $d^4$, so it may be understood that the outlet diameter, the channel diameter, its cross-section, as well as any combination of varying micro-machined cross-sections of the outlet channel and nozzle are an important factor in the structure of the liquid droplet spray device. In fact, this influence of the channel diameter size can be used to determine and vary the pressure drop and the velocity of the nebulized spray.

It is also known that the droplet diameter varies with certain physico-chemical properties of the liquid such as surface tension and viscosity. It is therefore important as shown in the cited prior art to be able to adapt the physical and electrical device parameters (frequency and amplitude) according to the liquid to be expelled and the desired droplet characteristics.

The applicant has now found that under certain circumstances the droplet size, the velocity and flow rate also vary with the voltage applied to the vibrating element. These conditions arise when the pressure drop across the outlet channel is low enough to allow for, for a given range, for example a mean diameter between 5 and 10 μm, the modulation of the droplet size, velocity and flow rate by the energy input alone, hence by the supply voltage.

Consequently, it seems possible to vary the geometric parameters of the outlet means in order to reach a certain droplet diameter, and then vary that size of the ejected droplets by varying the applied voltage.

It is however necessary to apply an innovative micro-machining technique to create a device that reaches such behaviour. Whilst semiconductor fabrication methods such as disclosed by applicant in documents EP-A-0 923 957 and EP-A-1 005 916, cited above, allow to etch the desired straight channels, it is difficult to further improve on the control of the pressure drop while at the same time retaining the control over the droplet size.

It is further known to create nozzle bodies having step-shaped channels. For example, the document EP-A-0 985 534 describes a method producing an inkjet printer head in which step-shaped nozzle channels are formed by dry etching techniques using induction coupled plasma (ICP) discharge. The nozzle formed has a cross-section made smaller stepwise toward the front end thereof. First of all, a resist film is formed on a surface of a silicon monocrystalline substrate. A first opening pattern is formed by half-etching the resist film at a portion corresponding to the rear, wider end of the nozzle channel. Next, a second opening pattern smaller than the first pattern is formed by full-etching the half-etched resist at a portion corresponding to the front, narrower end of the nozzle channel. Then, the nozzle channel is formed by applying dry etching by plasma discharge to the exposed second, narrower portion of the surface of the silicon monocrystalline substrate. After this, a second dry etching is carried out by full-etching the remaining hall-etched portion and by continuing the plasma etching of both the narrow and the wide portions until a through hole is obtained.

However, in this technique using plasma etching, notching inevitably occurs at the output ends of the nozzle channel. In fact, when etching the wider portion, the etching will continue in the narrower portion too due to etched ions located in this narrower portion of the nozzle channel. When reaching the end of the channel, a through hole is created, but the remaining ions will also etch away the edges of the through hole of the channel. Naturally, notched output nozzles complicate the droplet formation. In fact they favour the spreading of liquid in close vicinity of the nozzles and thus generate larger droplets than intended or prevent droplet formation all together by this wetting of the active surface.

It is, therefore, an object of the present invention to provide a method of manufacturing a liquid droplet spray device as well as the thus obtained device which overcomes the above-mentioned inconveniences and which allows for a controllable and programmable droplet size and flow rate.

It is another object of the present invention to provide such a device that is simple, reliable to manufacture, small in size and low in energy consumption and cost.

Thus, the present invention concerns a method of manufacturing a liquid droplet spray device and also a liquid droplet spray device as defined in the appended claims.

The present invention also concerns a method of manufacturing, a nozzle body for such a liquid droplet spray device, as also defined in the claims.

Thanks to the specific shape and arrangement of the outlet means of the spray device according to the present invention a programmable droplet size, velocity and flow rate of the expelled droplet may be obtained in a relatively simple manner. This can provide for an economic advantage, as the same device platform can be used to provide a different droplet size distribution, flow rate or exit velocity by simply changing the supply voltage applied to the piezoelectric vibrating element.

Other features and advantages of the liquid spray device according to the present invention will become clear from reading the following description, which is given solely by way of a non-limitative example thereby referring to the attached drawings in which:

FIG. 1 is a schematic cross-section of a prior art liquid droplet spray device, FIGS. 2*a* to 2*b* show schematic detailed views of the top substrate of the prior art liquid droplet spray device of FIG. 1, FIGS. 3*a* to 3*c* show schematic cross-sections of a preferred embodiment of the liquid droplet spray device according to the present invention, and FIG. 4 shows the steps of a method of fabricating, via an inventive differential plasma etch, a possible embodiment of a liquid droplet spray device according to the present invention.

FIG. 5 shows a bottom view of the first substrate incorporating a compression chamber and passive valves in a single space, and FIG. 6 shows steps of another method of manufacturing the present liquid droplet spiral device.

An example of a preferred embodiment will be described hereafter. The present invention thus concerns a method of manufacturing a liquid droplet spray device for nebulizing a liquid substance. The present invention also concerns the thus obtained spray device. For ease of understanding, the structure of the liquid droplet spray device itself will first be described while referring to FIGS. 3*a* to 3*c*. In principle, the spray device may be rather similar to the above described prior art spray device of the present applicant, except for the outlet means.

Thus, the present spray device also comprises a housing or a substrate. This housing may be formed of a first substrate 15 and a second substrate 16, in a rather similar manner as shown in FIG. 1. However, as shown in FIG. 3, first substrate 15 is placed upside down compared to first substrate 5 of FIG. 1. The housing may, however, only consist of a single substrate as will be explained in detail later on. Substrate 15 is provided with membrane sections 15*a* which are thinner sections of the substrate obtained by etching away parts of the substrate using appropriate methods of etch stop to guarantee homogeneous membrane thickness. The manner of obtaining such membrane sections is similar to that as described in the above referenced prior art document EP-A-0 923 957, and is well known to the skilled person from the field of semiconductor etching.

The etching may be done by wet or dry etching resulting in inclined or in straight sidewalls of the substrate portion leading away from the membrane section.

Figure 3B:
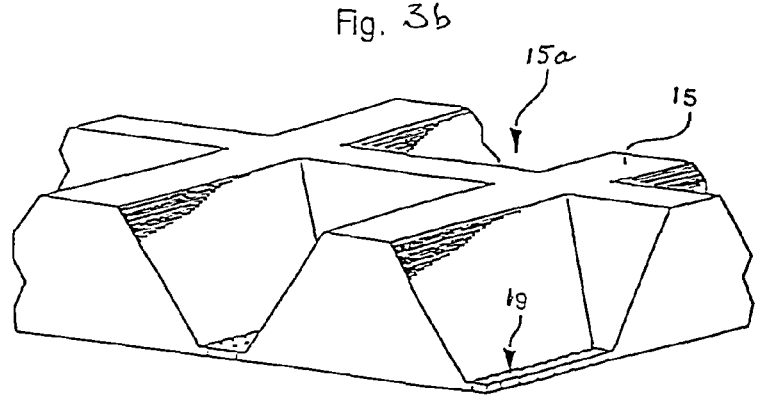
Figure 3C:
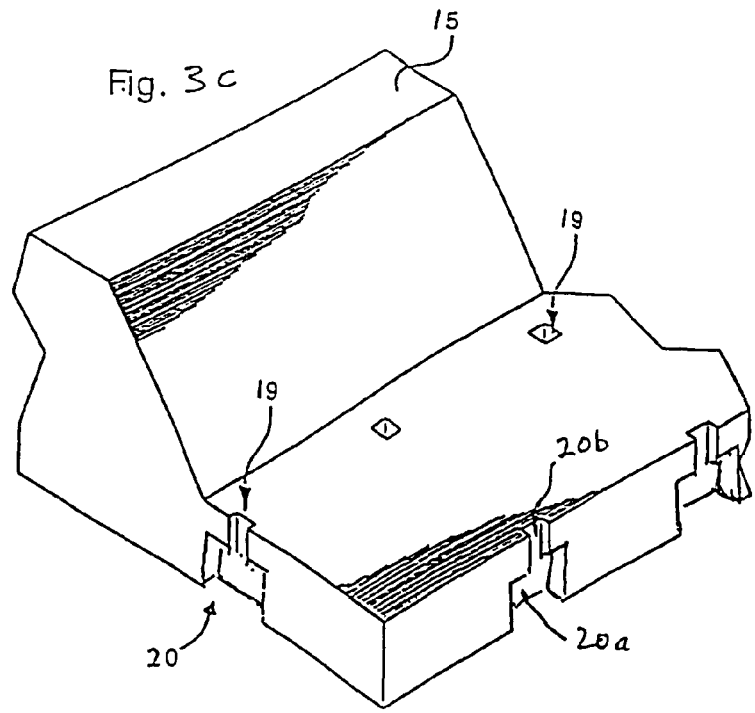
Figure 4:
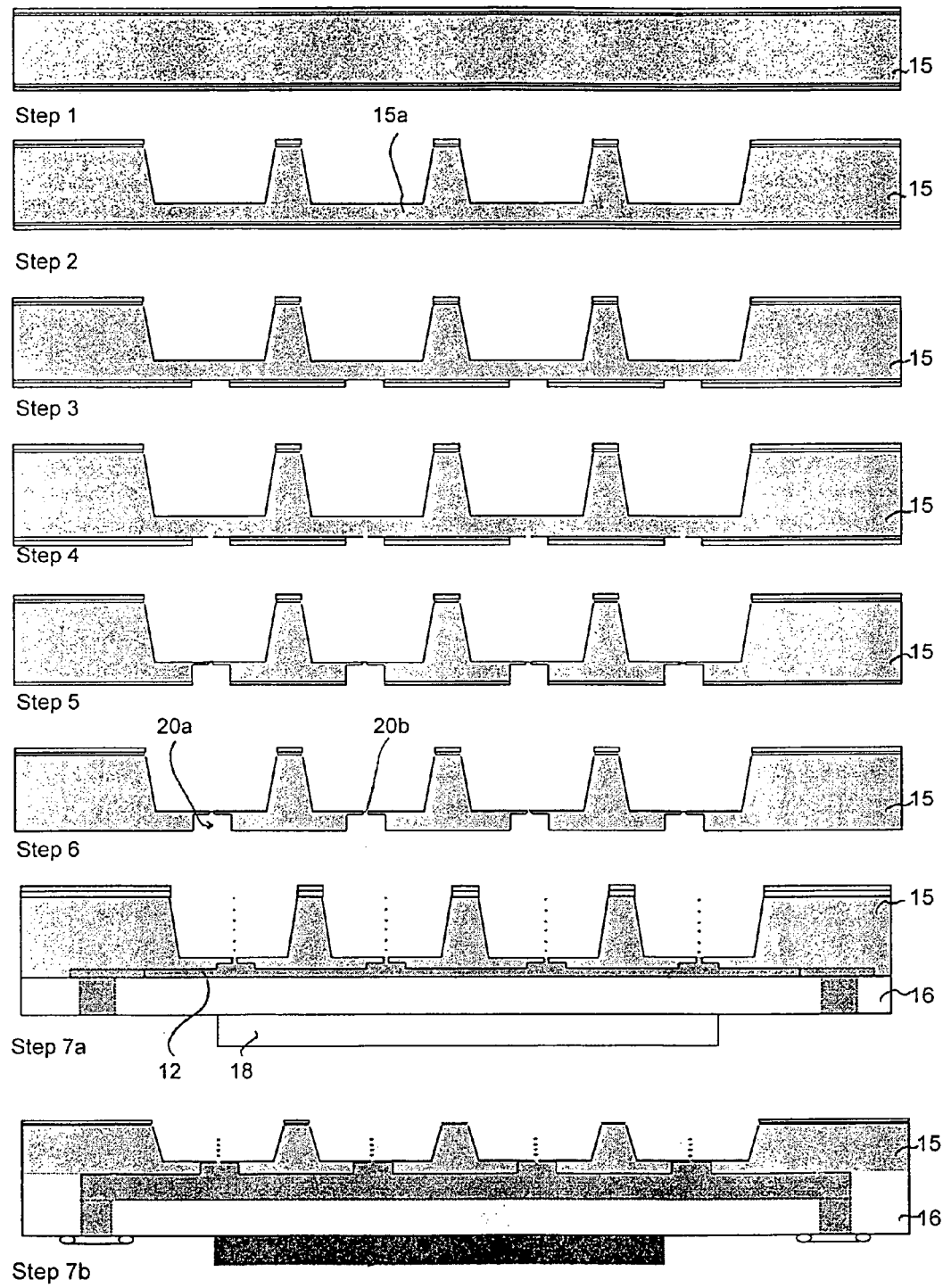

As can be seen in FIG. 3, a space 12 for containing the liquid substance is provided within the housing, between the two substrates 15 and 16. Such space can be created by etching a recess in the bottom surface of first substrate 15, the bottom substrate 16 presenting a flat surface towards the inside of space 12 such as shown in FIGS. 3 and 4. Such space can also be created in the bottom substrate 16 by wet or dry etch as will be described further on. The second substrate can also be advantageously replaced directly by the vibrating element 18 which for the purpose of protection has been suitably passivated as described in EP-A-0 923 957.

Figure 5:
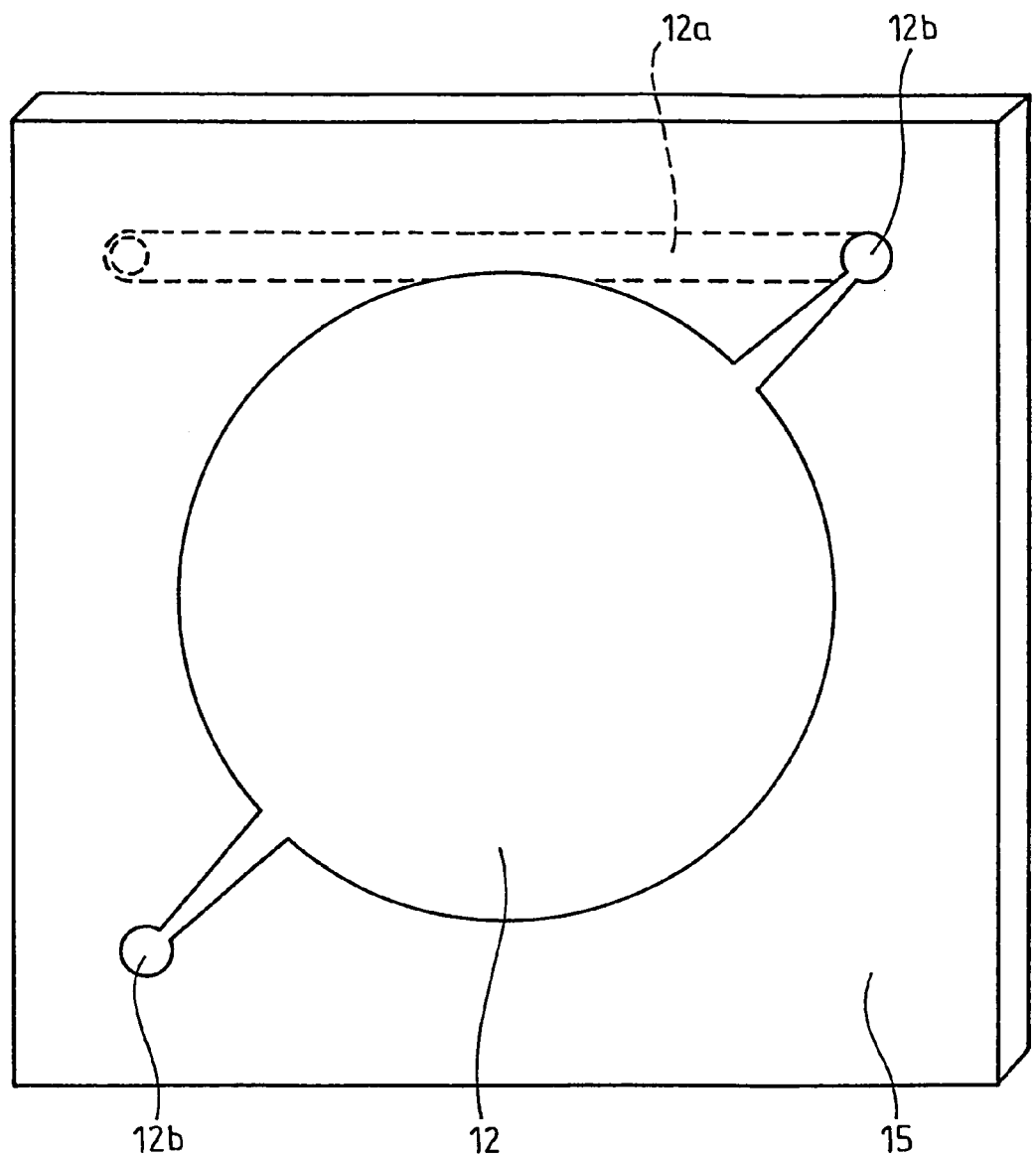

As shown in FIG. 5, space 12 is preferably of a round cross-section in order to facilitate filling and air evacuation and may incorporate a geometry for creating passive valves at its inlet and outlet. It may further be dimensioned or complemented, e.g. by connecting to an internal or external dosage buffer volume 12a, to contain a required dosage amount such that principal volume 12 together with buffer volume 12a correspond to a desired unit dose which may be larger than the internal volume of space 12. Thus, the desired unit dose may have a maximum dosage corresponding to the total volume of space 12, i.e. of principal volume 12 plus buffer volume 12a. In such a way space 12 is at first, e.g. before starting the droplet size generation, completely filled with the liquid to be expelled and remains filled for most of the operation when liquid is expelled roughly as fast as it is aspirated from buffer volume 12a, resulting in a stable operating condition for most of the operation, especially if the content of buffer volume 12a is larger than that of space 12. This buffer volume 12a allows for the spray device to be filled with a different dose for each intended use, ranging from the approximate volume of space 12 to the total volume of space 12 plus buffer volume 12a. Buffer volume 12a is realised preferably as a capillary meander or other geometrical configuration having a cross-section that facilitates capillary action thus providing easier priming of space 12 and buffer 12a. Further, appropriate means, such as a capillary channel 12b for supplying the liquid substance to and allowing exiting from space 12 is provided as known from the mentioned prior art. Such capillary channel can be advantageously configured to act as a passive valve, which is known as such, to allow for the liquid substance to enter and exit the space.

These features are highly advantageous when delivering for example insulin doses with a varying dosage volume depending on the glucometer reading at the time of use. It may of course also be advantageous in other applications where a variable dosage is indicated.

At least one outlet nozzle 19 and at least one output channel 20 for connecting space 12 to each outlet nozzle 19 are further provided in the thinner membrane section 15a of substrate 15. It is of course important that the output channel 20 has straight sidewalls so as to be able to define the pressure drop across the channel when a droplet is ejected, as already explained in detail in the above-mentioned prior art EP-A-0 923 957.

A vibrating element such as a piezoelectric element 18 is disposed on the housing to vibrate the liquid substance in space 12. Preferably, the vibrating element is arranged directly on the first substrate 15 or on a thinner section of the second substrate 16, e.g. acting as a membrane for transmitting a certain compression as well as the vibration to the liquid contained in space 12 and vibration to the total structure such as described in the above-mentioned prior art. When the liquid is excited at an appropriate frequency and under the appropriate pressure, it will be ejected as a spray of droplets through the outlet nozzles with a very low exit velocity. The preferred operation is at the fundamental resonance frequency of vibrating element 18 or at subsequent harmonics.

The transition of output channel 20 from space 12 to outlet nozzle 19 is not only straight, but is also step-shaped. As can be seen in FIG. 3c, output channel 20 consists of a lower part 20a and an upper part 20b. Lower part 20a of output channel 20 has a larger diameter than upper part 20b and can have the same or a different length as the upper part. Lower part 20a is arranged adjacent space 12 containing the liquid substance which is to be expelled.

Thanks to the stepped shape of the output channel 20, the excited liquid is forced at a higher pressure into the upper part 20b of the output channel. Thus, the eventual size of the droplet results mainly from the liquid volume that is contained in the smaller upper part 20b. Furthermore, the outlet nozzle is also straight without any notching at its periphery, thanks to the inventive method of manufacturing the spray device, as will be explained in detail further on.

As explained above, for a given liquid the diameter and the volume of the expelled droplet depend mainly on the pressure drop across the output channel and also on the applied voltage, amplitude and frequency.

Thus, as of a certain level of energy balance, the Applicant has found it to be possible, and practical, with the present structure to vary the droplet size by only varying the voltage applied to the vibrating element 18.

Further, thanks to the stepped shape of the output channel and the straight outlet nozzle, when the same power is used to create the droplet spray, a smaller droplet can be generated as compared to the mentioned prior art devices.

Experiments have shown that, for a given outlet channel diameter, if the applied voltage increases, the mean droplet size decreases.

Indeed, the following results were obtained:

| Applied voltage (V) | Mean droplet size (µm) |
| --- | --- |
| 5 | >18 |
| 10 | 10-12 |
| 20 | 7 |
| 30 | 3-4 |

Application has found that at virtually no input pressure, at 30 V and approximately 250 kHz applied to the vibrating element, more than 80% of the droplets were smaller than the diameter of the upper part of channel 20b.

It may thus be understood that it is possible to vary the droplet size, but with it the flow rate and also the exit velocity by varying the applied voltage so that a programmable platform for a liquid droplet spray device may be obtained. Consequently, it is possible to provide largely identical liquid droplet spray devices for different applications by simply varying the applied voltage. For example, the same spray device may be used as an inhaler for systemic, deep lung applications which require droplets of less than 3.3 µm or for upper lung treatment which requires droplets of less than 5.6 µm or for various types of liquids which require a different energy input to obtain the same droplet size.

According to the present invention, such a liquid droplet spray device is manufactured by using, the following method which is explained whilst referring to FIGS. 4 and 5. In principle, it is possible to etch two silicon wafers, one corresponding to a plurality of first substrates 15 and the other corresponding to a plurality of bottom substrates 16. However, it may be appreciated that the structure of the present liquid droplet spray device may also be realised bar sandwiching different materials such as Si, SiO$_2$, SiN, SU-8, metal, and the like, in suitable combinations, or by successive depositions of such materials. A detailed explanation of the manufacturing, of the first substrate 15 will be provided here. Indeed, this substrate has a more complicated shape than the bottom substrate.

As shown in step 1 of FIG. 4, first an oxide mask is deposited on both surfaces of a substrate which will form the first substrate 15.

Next, in step 2, the top surface is etched using for example a wet etching process, advantageously with an etch stopper (not shown) so as to obtain the thinner membrane sections 15a.

In step 3, two possibilities exist. In one case the oxide at the bottom surface of first substrate 15 is opened, defining large openings corresponding to the lower, wider, parts 20a of output channels 20, in this case space 12 is machined into substrate 16. In another case, the oxide is etched partially in order to shape space 12 into substrate 15 followed by an additional etch which defines the large openings corresponding to the lower, wider, parts 20a of output channels 20 (not fully shown in FIG. 4).

In step 4, after a photo-resist has been applied defining the small openings corresponding to upper parts 20b output channels 20, a plasma etching, preferably by using an ICP (Inductively Controlled Plasma) technique, of the silicon is carried out to obtain the shape of the small openings and is stopped at a suitable depth. After stripping of the resist followed by a differential plasma etching, the stepped configuration of output channels 20 with the desired proportions of the parts 20a and 20b is obtained without however opening the top or upper channel part 20b.

Indeed, according to the present invention, this differential plasma-etching step is stopped before the etching pierces, i.e. traverses the substrate. In fact, the present inventors have found that when piercing the substrate during such plasma-etching step, notching occurs resulting in slightly tapered outlet nozzles which could have a negative influence on the control of the droplet size and on its directivity when ejected from the nozzle.

In fact, a third plasma etch step is carried out either to create the space 12 locally into substrate 15 and to open upper channel part 20b or the third plasma etch step is carried out over the entire wafer surface in order to open upper channel part 20b in case that space 12 is to be machined into substrate 16, as shown respectively steps 7b or 7a of FIG. 4.

In both cases the surface to be etched is very large which results in a lower etching speed of the channel, i.e. the upper, narrow part 20b will be etched relatively slowly. Thus, the actual piercing will then occur at a very low speed which will avoid any notching effects.

Thus, according to the present invention, it is possible to avoid notching and thereby obtain straight through holes, i.e. straight step-shaped output channel by a correct choice of the surfaces to be differentially etched. In fact, the ratio of the large etching surface (corresponding to space 12) to the small etching surface (corresponding to the upper, narrow channel part 20b) should be chosen such that the etching speed will be low enough in the small etching surface that notching is avoided.

After that last differential plasma etch cycle the wafer is turned and the top surface of the first substrate 15 is etched with the same plasma etcher, preferably in only one step which is stopped in the passivation mode in order to provide a hydrophobic quality of that top surface.

This innovative etching process is called differential etching because the larger exposed surface will be etched faster than the smaller exposed surface, i.e. the "bottom" of the narrow channel part. During this etching step, the narrower channel will be etched to become slightly longer so as to eventually correspond to the actual desired dimensions of upper part 20b of output channel 20, but this narrower part will also be "pushed forward" with respect to the larger opened portion of the silicon by the etching so as to eventually pierce the substrate with the third plasma-etching step.

A skilled person will readily realise that the thinner section for accommodating the piezoelectric element may be obtained by machining it into silicon or Pyrex wafers. This second substrate may also be directly replaced by a suitably passivated vibrating element 18. Any further shape changes may also be conceived by applying the usual techniques in the field.

Finally, in a further step, indicated as step 7a and 7b in FIG. 4, the bottom surface of first substrate 15 and the top surface of second substrate 16 are bonded together, preferably by using anodic bonding so as to form the housing of the liquid droplet spray device thereby enclosing space 12.

As mentioned above, it is possible to apply a further differential etching step to first substrate 15 to etch away a part of first substrate 15 so as to obtain space 12 directly in first substrate 15. It is further also possible to etch, either at the same time or in a separate step, the buffer volume 12a and/or passive valves 12b. Then, second substrate 16 may be applied to first substrate 15 so as to close space 12. However, as also mentioned briefly above, instead of using the second substrate, it is also possible to directly bond the vibrating element 18, whose surface is preferably suitably treated and protected beforehand, to first substrate 15 so as to enclose space 15.

A selective hydrophilic coating, such as an amorphous material such as SiO2, may further be applied to provide a protective layer around the inside surface of space 12 and/or of the output channels 20 to avoid any contamination of the liquid substance by the material of these surfaces and to improve wettability in certain parts. This hydrophilic coating which may be applied as a selective, patterned coating and is advantageously coupled with a selective, patterned hydrophobic coating in certain areas of space 12 and on the outside of first substrate 15.

Alternatively to applying a plasma etch, using the same production equipment as for the innovative differential plasma etching process described earlier, on the top surface of substrate 15 and stopping it in the passivation mode, a hard amorphous carbon film may be provided on first substrate 15 in order to maintain the protective aspect of its surfaces and at the same time to reduce the internal and external stiction due to capillary forces in space 12, and especially on the outside of substrate 15. This hard amorphous carbon film, e.g. diamond-like carbon (DLC) or fluorinated DLC (F*DLC) is provided, preferably in a selective patterned manner in these areas. Other hydrophobic coatings such as nitride or Teflon might be deposited by spinning and curing, by plasma or by other suitable methods. Such selective film coating also allows for a more complete emptying of space 12 and avoids stiction of liquid on the outside surface of substrate 15 due to low surface energy.

The present Applicant has found that such surface property specific coating influences and improves droplet size dispersion and provides an even better mono-dispersive pattern released by the spray device. These coatings may be carried out as described in the document U.S. Pat. No. 5,462,839.

Another method of manufacturing the present liquid droplet spray device, and/or the nozzle body thereof, will now be described while referring, to FIGS. 6a and 6b. Only steps that are different from those described above will be explained in detail. In fact, following steps 1 and 2 shown in FIG. 4, so as to obtain the thinner membrane sections 15a of first substrate 15, it is possible to directly etch, in any conventional manner, the bottom surface of a membrane section to obtain a channel, the diameter of which corresponds substantially to the narrow upper portion 20b of the output channel 20. Next, the whole wafer surface is etched as described earlier in order to pierce the substrate without notching at the channel outlet nozzle 19. Thus, a channel traversing the membrane section 15a is obtained, as shown in step 1 of both FIGS. 6a and 6b.

Following this, the inner sidewalls of the channel are covered with a protective layer such as all oxide as shown in step 2 of FIGS. 6a and 6b. Then, a resist film is formed on the bottom surface of first substrate 15 and an opening is defined corresponding to the lower wider portion 20a of output channel 20 (not shown). Then, the lower portion 20a is formed by etching first substrate 15 so as to obtain the lower portion 20a of the output channel, as shown in step 3 of FIGS. 6a and 6b.

At this point, similar to what has been described above, there are 2 possibilities depending on into which substrate space 12 is to be integrated.

In a first possibility the oxide in the narrow upper portion 20b is removed, as shown in step 4 of FIG. 6a, and first substrate 15 is substantially ready to be bonded with second substrate 16 in which space 12 has been machined as described earlier.

In the other version, the sidewall is of the lower portion 20a are also covered with a protective layer same as the oxide protecting the inner sidewalls of the upper portion 20b, as shown in step 4 of FIG. 6b. Then, another resist is applied on the bottom surface of first substrate 15 and an opening is defined corresponding to the recess which is to constitute space 12 (not shown). After this, the bottom surface of first substrate 15 is again etched so as to obtain the recess, forming space 12, as shown in step 5 of FIG. 6b. Then the oxide is removed as shown in step 6 of FIG. 6b.

In this manner, it is thus also possible to obtain the same structure of the liquid droplet spray device according to the present invention having a step-shaped output channel with a recess whereby the outlet nozzle at the end of the output channel does not show notching influences when the substrate is pierced. Although in this alternative second method, more steps are required than in the above-described first method, the steps used here can be conventional steps thus allowing for a reliable manufacturing of the liquid droplet spray device.

Having described a preferred embodiment of this invention, it will now be apparent to one of skill in the art that other embodiments incorporating its concept may be used. It is felt, therefore, that this invention should not be limited to the disclosed embodiment, but rather should be limited only by the scope of the appended claims.

For example, the same liquid droplet spray device may not only be used for an inhaler in respiratory therapies, but it may generally be used for creating nebulized liquids of different physico-chemical compositions, e.g. using aqueous or alcoholic or other liquid substances.

The invention claimed is:

1. A programmable liquid droplet spray device for atomising a liquid substance, comprising:

(a) a housing comprising a first substrate having a first surface and a second surface, wherein said first substrate has at least one membrane section that is thinner than a rest of said first substrate, and said first substrate has a cavity formed on the first surface that at least partially defines said at least one membrane section;

(b) a space within the housing adapted to contain the liquid substance;

(c) a first supply disposed to supply said liquid substance to said space, wherein the second surface of the first substrate is directed toward said space;

(d) an outlet arranged in said membrane section and comprising at least one outlet nozzle arranged in the first surface of said first substrate and at least one output channel connecting said space to said at least one outlet nozzle;

(e) a vibrating element disposed to vibrate liquid in said space so as to eject said liquid substance as an atomized spray through said at least one outlet nozzle; and (f) a voltage supply connected to the vibrating element, wherein said at least one output channel has a stepped shape having a lower portion and an upper portion, and said lower portion is arranged adjacent said space and is of larger diameter than said upper portion, and said output channel has straight and parallel side walls, and in that said rest of said first substrate comprises sections that are thicker than said membrane section and that are located on the side of the first surface of said first substrate, and wherein droplet size of the atomized spray through said at least one outlet nozzle is variable by varying only the applied voltage so that the liquid droplet spray device is a programmable platform that generates the atomized spray comprising droplets of a selected size based on selected applied voltage.

2. A programmable liquid droplet spray device according to claim 1, further characterised in that said rest of said first substrate consists of thicker sections having sidewalls leading away from said at least one membrane section.

3. A programmable liquid droplet spray device according to claim 2, further characterised in that said first substrate has a recess in the second surface of said first substrate that at least partially defines said space.

4. A programmable liquid droplet spray device according to claim 2, wherein said housing further comprises a second substrate, and wherein said space is provided in said second substrate.

5. A programmable liquid droplet spray device according to claim 2, further comprising a passive valve arranged in physical combination with said space for facilitating homogeneous operation of said device by providing a homogenous filling of said space with said liquid substance.

6. A programmable liquid droplet spray device according to claim 2, wherein said space consists of a principal volume and a buffer volume, said buffer volume being dimensioned such that the total volume of said principal volume together with said buffer volume corresponds to a maximum dosage, so that a desired variable dosage depending on the specific usage of said spray device may be contained in said space, said variable dosage being equal to or less than said maximum dosage.

7. A programmable liquid droplet spray device according to claim 1, further characterised in that said first substrate has a recess in the second surface of said first substrate that at least partially defines said space.

8. A programmable liquid droplet spray device according to claim 7, wherein said housing further comprises a second substrate, and wherein said space at least partially defined by said recess is closed off by said second substrate.

9. A programmable liquid droplet spray device according to claim 8, further comprising a passive valve arranged in physical combination with said space for facilitating homogeneous operation of said device by providing a homogenous filling of said space with said liquid substance.

10. A programmable liquid droplet spray device according to claim 8, wherein said space consists of a principal volume and a buffer volume, said buffer volume being dimensioned such that the total volume of said principal volume together with said buffer volume corresponds to a maximum dosage, so that a desired variable dosage depending on the specific usage of said spray device may be contained in said space, said variable dosage being equal to or less than said maximum dosage.

11. A programmable liquid droplet spray device according to claim 7, further comprising a passive valve arranged in physical combination with said space for facilitating homogeneous operation of said device by providing a homogenous filling of said space with said liquid substance.

12. A programmable liquid droplet spray device according to claim 7, wherein said space consists of a principal volume and a buffer volume, said buffer volume being dimensioned such that the total volume of said principal volume together with said buffer volume corresponds to a maximum dosage, so that a desired variable dosage depending on the specific usage of said spray device may be contained in said space, said variable dosage being equal to or less than said maximum dosage.

13. A programmable liquid droplet spray device according to claim 1, further characterised in that said vibrating element is round and of a smaller cross-section than said space and is arranged to operate at a fundamental resonance frequency or subsequent harmonics so as to eject said liquid substance as the atomized spray through said at least one outlet nozzle.

14. A programmable liquid droplet spray device according to claim 13, further comprising a passive valve arranged in physical combination with said space for facilitating homogeneous operation of said device by providing a homogenous filling of said space with said liquid substance.

15. A programmable liquid droplet spray device according to claim 13, wherein said space consists of a principal volume and a buffer volume, said buffer volume being dimensioned such that the total volume of said principal volume together with said buffer volume corresponds to a maximum dosage, so that a desired variable dosage depending on the specific usage of said spray device may be contained in said space, said variable dosage being equal to or less than said maximum dosage.

16. A programmable liquid droplet spray device according to claim 1, wherein said housing further comprises a second substrate, and wherein said space is provided in said second substrate.

17. A programmable liquid droplet spray device according to claim 16, further comprising a passive valve arranged in physical combination with said space for facilitating homogeneous operation of said device by providing a homogenous filling of said space with said liquid substance.

18. A programmable liquid droplet spray device according to claim 16, wherein said space consists of a principal volume and a buffer volume, said buffer volume being dimensioned such that the total volume of said principal volume together with said buffer volume corresponds to a maximum dosage, so that a desired variable dosage depending on the specific usage of said spray device may be contained in said space, said variable dosage being equal to or less than said maximum dosage.

19. A programmable liquid droplet spray device according to claim 1, further comprising a passive valve arranged in physical combination with said space for facilitating homogeneous operation of said device by providing a homogenous filling of said space with said liquid substance.

20. A programmable liquid droplet spray device according to claim 19, wherein said space consists of a principal volume and a buffer volume, said buffer volume being dimensioned such that the total volume of said principal volume together with said buffer volume corresponds to a maximum dosage, so that a desired variable dosage depending on the specific usage of said spray device may be contained in said space, said variable dosage being equal to or less than said maximum dosage.

21. A programmable liquid droplet spray device according to claim 1, wherein said space consists of a principal volume and a buffer volume, said buffer volume being dimensioned such that the total volume of said principal volume together with said buffer volume corresponds to a maximum dosage, so that a desired variable dosage depending on the specific usage of said spray device may be contained in said space, said variable dosage being equal to or less than said maximum dosage.

22. A programmable liquid droplet spray device according to claim 1, wherein the outlet arranged in said membrane section comprises a plurality of outlet nozzles arranged in the first surface of said first substrate, wherein each outlet nozzle is provided with an output channel connecting the outlet nozzle to said space, wherein each output channel has a stepped shape having a lower portion and an upper portion, said lower portion being arranged adjacent said space and being of larger diameter than said upper portion, said output channel having straight and parallel side walls.

23. A programmable liquid droplet spray device according to claim 1, further comprising a selective hydrophilic coating disposed on a surface of the device to provide a protective layer.

24. A programmable liquid droplet spray device according to claim 23, wherein the selective hydrophilic coating is disposed to provide a protective layer around an inside surface defining the space.

25. A programmable liquid droplet spray device according to claim 23, wherein the selective hydrophilic coating is disposed to provide a protective layer around said at least one output channel.

26. A programmable liquid droplet spray device according to claim 23, wherein the selective hydrophilic coating is disposed to provide a protective layer around the inside surface defining the space and around said at least one output channel.

27. A programmable liquid droplet spray device according to claim 1, wherein the programmable liquid droplet spray device generates the atomized spray comprising droplets of the selected size based on the selected applied voltage so that varying the applied voltage varies droplet size of the atomized spray through said at least one outlet nozzle and varies the flow rate and the exit velocity of the atomized spray.

28. A liquid droplet spray device for atomising a liquid substance, comprising:
(a) a housing comprising a first substrate having a first surface and a second surface, wherein said first substrate has at least one membrane section that is thinner than a rest of said first substrate, and said first substrate has a cavity formed on the first surface that at least partially defines said at least one membrane section;

(b) a space within the housing adapted to contain the liquid substance;
(c) a first supply disposed to supply said liquid substance to said space, wherein the second surface of the first substrate is directed toward said space;
(d) an outlet arranged in said membrane section and comprising at least one outlet nozzle arranged in the first surface of said first substrate and at least one output channel connecting said space to said at least one outlet nozzle;
(e) a vibrating element disposed to vibrate liquid in said space so as to eject said liquid substance as an atomized spray through said at least one outlet nozzle;
(f) a voltage supply connected to the vibrating element;
(g) a passive valve arranged in physical combination with said space for facilitating homogeneous operation of the device by providing a homogenous filling of said space with the liquid substance; and
(h) a selective hydrophilic coating disposed on a surface of the device to provide a protective layer,
wherein said at least one output channel has a stepped shape having a lower portion and an upper portion, wherein said lower portion is arranged adjacent said space and is of larger diameter than said upper portion, and said output channel has straight and parallel side walls, and in that
said rest of said first substrate comprises sections that are thicker than said membrane section and that are located on the side of the first surface of said first substrate, and wherein droplet size of the atomized spray through said at least one outlet nozzle is variable by varying only the applied voltage, wherein said vibrating element is round and of a smaller cross-section than said space and is arranged to operate at a fundamental resonance frequency or subsequent harmonics so as to eject said liquid substance as the atomized spray through said at least one outlet nozzle, and wherein
said space consists of a principal volume and a buffer volume, and said buffer volume is dimensioned so that the total volume of said principal volume together with said buffer volume corresponds to a maximum dosage, so that a desired variable dosage depending on the specific usage of said spray device may be contained in said space, wherein said variable dosage is equal to or less than said maximum dosage.

29. Liquid droplet spray device for atomising a liquid substance, comprising:
a housing comprising a first substrate having a first surface and a second surface, having at least one membrane section that is thinner than a rest of said first substrate, and having a cavity on the first surface that at least partially defines said at least one membrane section, wherein a hard amorphous carbon film is disposed on the first surface;
a space within the housing adapted to contain the liquid substance;
a first supply disposed to supply said liquid substance to said space, the second surface of the first substrate being directed toward said space;
an outlet arranged in said membrane section and comprising at least one outlet nozzle arranged in the first surface of said first substrate and at least one output channel connecting said space to said at least one outlet nozzle;
a vibrating element disposed to vibrate liquid in said space so as to eject said liquid substance as an atomized spray through said at least one outlet nozzle;
a voltage supply connected to the vibrating element; and
a passive valve arranged in physical combination with said space for facilitating homogeneous operation of the device by providing a homogenous filling of said space with the liquid substance,
characterised in that said at least one output channel has a stepped shape having a lower portion and an upper portion, said lower portion being arranged adjacent said space and being of larger diameter than said upper portion, said output channel having straight and parallel side walls, and in that
said rest of said first substrate comprises sections that are thicker than said membrane section and that are located on the side of the first surface of said first substrate, and wherein droplet size of the atomized spray through said at least one outlet nozzle is variable by varying only the applied voltage, wherein said vibrating element is round and of a smaller cross-section than said space and is arranged to operate at a fundamental resonance frequency or subsequent harmonics so as to eject said liquid substance as the atomized spray through said at least one outlet nozzle, and wherein
said space consists of a principal volume and a buffer volume, and said buffer volume is dimensioned such that the total volume of said principal volume together with said buffer volume corresponds to a maximum dosage, so that a desired variable dosage depending on the specific usage of said spray device may be contained in said space, wherein said variable dosage is equal to or less than said maximum dosage.

30. A liquid droplet spray device for atomising a liquid substance, comprising:
(a) a housing comprising a first substrate having a first surface and a second surface, wherein said first substrate has at least one membrane section that is thinner than a rest of said first substrate, and said first substrate has a cavity formed on the first surface that at least partially defines said at least one membrane section;
(b) a space within the housing adapted to contain the liquid substance;
(c) a first supply disposed to supply said liquid substance to said space, wherein the second surface of the first substrate is directed toward said space;
(d) an outlet arranged in said membrane section and comprising at least one outlet nozzle arranged in the first surface of said first substrate and at least one output channel connecting said space to said at least one outlet nozzle;
(e) a vibrating element disposed to vibrate liquid in said space so as to eject said liquid substance as an atomized spray through said at least one outlet nozzle;
(f) a voltage supply connected to the vibrating element;
(g) a passive valve arranged in physical combination with said space for facilitating homogeneous operation of the device by providing a homogenous filling of said space with the liquid substance; and
(h) a selective hydrophilic coating disposed on a surface of the device to provide a protective layer,
wherein said at least one output channel has a stepped shape having a lower portion and an upper portion, wherein said lower portion is arranged adjacent said space and is of larger diameter than said upper portion, and said output channel has straight and parallel side walls, and in that
said rest of said first substrate comprises sections that are thicker than said membrane section and that are located on the side of the first surface of said first substrate, and wherein droplet size of the atomized spray through said at least one outlet nozzle is variable by varying only the applied voltage, wherein said vibrating element is round and of a smaller cross-section than said space and is arranged to operate at a fundamental resonance frequency or subsequent harmonics so as to eject said liquid substance as the atomized spray through said at least one outlet nozzle, and wherein said space consists of a principal volume and a buffer volume, and said buffer volume is dimensioned so that the total volume of said principal volume together with said buffer volume corresponds to a maximum dosage, so that a desired variable dosage depending on the specific usage of said spray device may be contained in said space, wherein said variable dosage is equal to or less than said maximum dosage, wherein the liquid droplet spray device is a programmable liquid droplet spray device that generates the atomized spray comprising droplets of a selected size based on selected applied voltage, wherein varying the applied voltage varies droplet size of the atomized spray through said at least one outlet nozzle and varies the flow rate and the exit velocity of the atomized spray.

* * * * *